Jan. 31, 1961 M. VAN RENSSELAER Plant Pat. 2,015
MAGNOLIA GRANDIFLORA TREE
Filed March 28, 1960
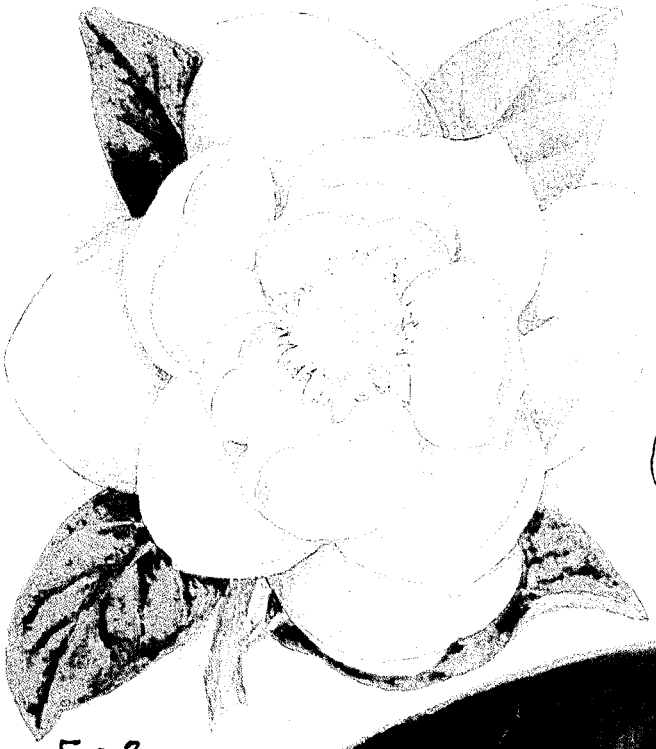
FIG. 2
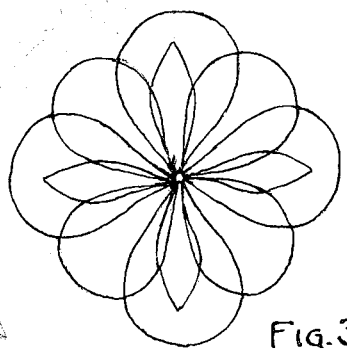
FIG. 3
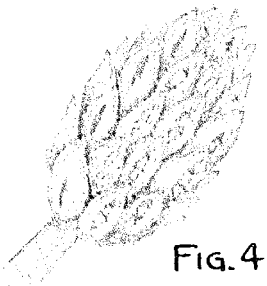
FIG. 4
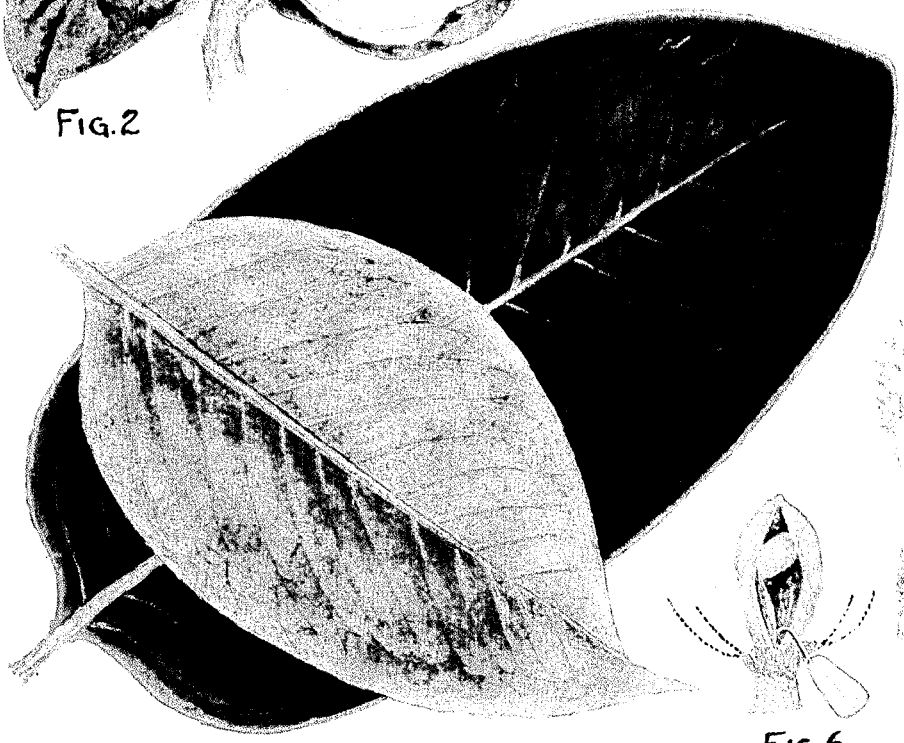
FIG. 1
FIG. 5
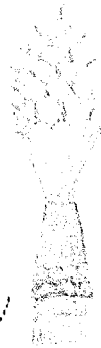
FIG. 6
WITNESS
Addison E. Avery
INVENTOR
Maunsell Van Rensselaer
by Rummler & Snow
ATTYS.

United States Patent Office

Plant Pat. 2,015

Patented Jan. 31, 1961

2,015

MAGNOLIA GRANDIFLORA TREE

Maunsell Van Rensselaer, Saratoga, Calif., assignor to Saratoga Horticultural Foundation, Inc., Saratoga, Calif., a corporation of California Filed Mar. 28, 1960, Ser. No. 18,203

1 Claim. (Cl. 47—60)

This disclosure concerns a new and distinct variety of *Magnolia grandiflora* tree discovered by me at the growing grounds of the Saratoga Horticultural Foundation at Saratoga, California. The new variety originated as a selected seedling of cultivated *Magnolia grandiflora* (unpatented), the pollen parent being unknown, and has been asexually reproduced by me at Saratoga, California, by cuttings, budding, and grafting, but mainly by grafting scions of the new variety on seedling-grown root stock of *Magnolia grandiflora.*

Asexual propagation of the new variety has been carried on continuously, under my direction, since 1952 and in all cases the novel and distinctive characteristics of the new variety have been found to hold true to the original plant.

Among the features of the new variety which make it distinctive from all others are its extraordinarily robust, upright and densely clothed form; its large leathery leaves having light green mid-ribs and primary veins prominently displayed against a dark, glossy green surface and a light green band around the leaf margin; and a coating, on the underside of the leaf, of silky, dark rusty brown tomentum which provides a remarkably distinctive effect when the tree is viewed in the late afternoon sun.

Other distinctions of the new variety reside in the robust branches of the new tree which ascend sharply from the trunk to form an oval upright crown making the new variety particularly desirable for streetside planting; and in its flowers, which are of extraordinarily large size, are exceptionally beautiful, and have four concave petaloids and eight concave petals arranged alternately in ranks of four, one above the other. A further distinction is that grafted plants of the new variety bloom during the first year, and each year thereafter. Plants a few years old bloom continuously from the middle of May to the middle of August and then intermittently through September and into October.

The distinctive features of the foliage and blooms of the new variety are shown in full color in the accompanying illustration in which:

Figure 1 is a view showing the top and bottom sides of mature leaves of the new plant variety and indicating a typical range of leaf size occurring on the same tree.

Figure 2 is a full face view of a bloom of the new plant variety, in the final stages of development, showing juvenile leaves in the background to illustrate their top and bottom side coloring.

Fig. 3 is a diagrammatic sketch, in ink, to illustrate the alternate rank arrangement of the petals and petaloids in a typical bloom.

Fig. 4 is a view showing a ripened fruit cone and illustrating the nature and arrangement of the seed pods.

Fig. 5 is a view showing a typical unripened fruit cone and spindle after the petals of the bloom have fallen, and Fig. 6 is a view showing a single ripened seed pod with a seed hanging out therefrom, the dotted lines indicating the outline of the full fruit cone.

The following is a detailed description of my new and distinct variety of *Magnolia grandiflora* tree:

Parentage: Seedling of *Magnolia grandiflora* (unpatented), pollen parent unknown.

Form: Tree.

*Growth.*—Vigorous, robust, upright with compact and dense crown. Hardy to 15° F. Ultimate size unkown, but in California climate should reach 40 to 50 feet. Rate of growth is 18 to 30 inches annually.

*Trunk.*—Stocky and smooth with bark having thin appressed scales.

*Branches.*—Light grey in color with smooth bark having thin appressed scales. Branches are stout, densly arranged and ascend sharply from the trunk to form an oval upright crown. During the period of rapid growth, the stout, terete branchlets are coated with short, thick, silvery tomentum which is soon deciduous, thereby exposing a dark green shiny bark.

Foliage: Heavy, very thick and leathery.

*Shape.*—Elliptic or broadly elliptic to oval-ovate, slightly acute, and tapering or rounded at the base. The leaf margins are smooth and unbroken.

*Size.*—Mostly larger than those of the species, blade is variable in length from 5 to 10 inches, and variable in width from 3 to 6 inches. In contrast the leaves on other clones of *Magnolia grandiflora* are smaller and more uniform in size.

*Color.*—Upper surface is dark glossy green and glabrous, with prominent light green mid-rib and primary veins conspicuously displayed and with a prominent light green hyaline margin. The under surface is tomentose and of a dark rusty brown.

*Petioles.*—½ to ⅞ inch in length and coated with a dark rusty tomentum. Petioles and twigs are both stout and vigorous.

Flower bud:

*Size.*—4 to 5 inches long and approximately 2 to 3 inches in diameter.

*Form.*—Narrowly ovoid with a long and pointed body.

*Growth.*—The bud is enclosed in a stipular spathe which splits longitudinally and is deciduous over a period of 2 or 3 days when the flower is ready to open. The spathe is coated with a soft brown tomentum and the petaloids and petals are imbricated in the bud. The bud opens slowly over several days depending on weather.

*Color.*—The bud is creamy white as the sepals and the petals begin to unfurl.

*Peduncle.*—Erect and stout about ½ inch in diameter and about ¾ inch to 1 inch in length. The peduncle is brownish green in color and is covered with a soft, brown tomentum.

Flower: Blooms continuously from mid-May to mid-August, profusely through June and July, and then intermittently and sparsely through September and sometimes through October.

*Color.*—Creamy white.

*Size.*—Very large, 10 inches to 14 inches in diameter.

*Form.*—Single, and terminally borne. Shape: Vase shaped, 5 to 6 inches deep upon first opening, flattening to cup shape and then to bowl or saucer shape as the opening process proceeds, the opening process taking several days depending on the weather. The flower has a center spindle or receptacle 1½ inches high on which stamens and pistils are imbricated (Fig. 2).

*Petalage.*—8 petals, arranged in two alternating ranks or tiers above a set of 4 petaloid sepals. The petals are broadly spatulate and concave in form, and are of a creamy white color throughout. The petals stay on the stem for 3 to 5 days, or sometimes longer, depending on the weather.

*Petaloids.*—4 in number and of the same color as the petals.

*Texture.*—Soft and leathery. Velvety in appearance.

*Discoloration.*—Petals turn brown and are shortly thereafter deciduous.

*Fragrance.*—Very fragrant. One cut flower perfumes an entire house.

*Lasting quality.*—3 to 5 days, or more, on plant depending on weather; 3 to 5 days as a cut flower. Excessive heat with low humidity shortens the life span of the flower. The flower does very well in conditions of heat with high humidity.

Genital organs:

*Stamens.*—Golden yellow in color and imbricated in many ranks upon the base of the receptacle (Fig. 2). Anthers—strap-shaped, ⅝ to ¾ inch long, and cream colored with purplish base. Very abundant and indefinite in number. Filaments—shorter than anthers and of same color. Pollen—golden yellow in color.

*Pistils.*—Indefinite in number and densely imbricated on the receptacle. Style is short, recurved and stigmatose on the inner face.

*Stigmas.*—Golden yellow in color.

*Ovaries.*—Single celled and fleshy.

Fruit:

*Shape.*—Fleshy, narrowly ovate cone, 3 to 4¾ inches long and 2 to 2½ inches wide at base, tapering slightly to a blunt apex and standing upright on sturdy peduncles about 1 inch long. Fruit body is comprised of coalescent two-seeded carpels.

*Color.*—When green the whole fruit is coated with silvery tomentum, giving the cone a silvery tone. As the fruit ripens the exposed portions turn to tints of scarlet before dehiscense in October and November and thence to a rusty brown leathery texture at maturity (Fig. 4) when the seeds slowly emerge from the carpels.

*Seeds.*—Upon emergence from the carpels, the seeds are suspended by long slender white cords before falling (Fig. 6). The seeds are ½ inch long, triangular in shape and two are formed in each carpel. The color is a bright glossy red.

The colors of the flower, fruit, seeds and foligae are shown in the following tubulation, according to Maerz and Paul's Dictionary of Color and the Horticultural Color Chart of the British Horticultural Society as indicated.

*Magnolia grandiflora*

COLOR CHART

| | Maerz and Paul | | | Hortic. Color Chart | | |
|---|---|---|---|---|---|---|
| | Plate | Letter | Number | Sheet | Name | Number |
| Flower: Petals, White | 9 | A | 1 | | | |
| (Fig. 2) Stamens, Yellow | 9 | K | 5 | | | |
| Leaves: Juvenile (Fig. 2) top | | | | 0960 | Spinach Green. | 0960/3 |
| (Fig. 2) Juvenile bottom side (Tomentum-rustry brown color varies). | 14 | A, B, C | 11, 12 | | | |
| (Fig. 1)— | | | | | | |
| Mature Leaf—top | | | | 0960 | do | 0960/2 to 0960+ |
| Mature Leaf—mid-rib and veins | 18 | L | 3 | | | |
| Mature Leaf—Bottom (Tomentum color varies). | 14 to 14 | L to L | 8 to 12 | | | |
| Mature Leaf—Top margin | 18 | L | 5 | | | |
| Fruit—Carpels: | | | | | | |
| (Fig. 4)— | | | | | | |
| Olive yellow green | 12 | K | 6 | | | |
| tipped with | 3 | K | 8 | | | |
| to | 3 | L | 9 | | | |
| Seeds—Unripe | 1 | A | 9 | | | |
| (Fig. 6)— | | | | | | |
| Seeds—Ripe | 1 | L | 12 | | | |
| Seed thread | 1 | A | 1 | | | |
| (Fig. 5) Spindle—Stamen receptacle | 6 | A | 6 | | | |

A most distinctive and outstanding characteristic of my new and improved variety of *Magnolia grandiflora* tree is the extraordinarily large size and attractive coloring of its leaves and the very large size of its flowers which are 1½ to 2 times the size of the blooms produced by a normal plant of the species. The tree is very robust and, being densely clothed with abundant foliage of unusual size and coloring, and having a uniformly shaped oval upright crown, is particularly advantageous for decorative and street side planting. The dark glossy green of the top side of the leaves, together with the prominent markings provided by the mid-rib, veins and marginal band of contrasting color, is most attractive and the coating of silky, dark brown tomentum on the underside of the leaves, which varies somewhat between the young and old leaves, affords an unusual and pleasing effect.

Another distinction of my new variety of *Magnolia grandiflora* tree is the exceptionally beautiful structure of the flower resulting from the rank upon rank arrangement of 8 petals and 4 petaloids which arrangement is utterly consistent throughout all of the blooms of each tree and in all of the progenies of the new variety that have been produced.

Having now disclosed my discovery, I claim:

A new, distinct and improved variety of *Magnolia grandiflora* tree substantially as shown and described, characterized particularly by its unusually large and abundant foliage having a dark glossy green color on the upper sides of the leaves and a dark rusty brown tomentum on the underside of the leaves, the conspicuously displayed light green mid-rib and primary veins of the leaves, and the light green hyaline margin of the leaves; the extraordinarily large size of its blooms, and the uniform arrangement of the petals in alternating tiers of four; the erect densely clothed growth of the tree with its sharply ascending branches to form an oval upright crown; its sturdy, hardy and unusually rapid growth habits; and the consistency of its growth form, foliage, size and coloring.

No references cited.